United States Patent
Chung et al.

(10) Patent No.: US 9,499,505 B2
(45) Date of Patent: Nov. 22, 2016

(54) PROCESS FOR THE EPOXIDATION OF OLEFINS

(71) Applicant: Chang Chun Plastics Co., Ltd., Hukou Township (TW)

(72) Inventors: Sung-Kuang Chung, Hukou Township (TW); Ping-Chieh Wang, Hukou Township (TW); An-Pang Tu, Hukou Township (TW); Kuen-Yuan Hwang, Hukou Township (TW)

(73) Assignee: Chang Chun Plastics Co., Ltd. (TW)

( * ) Notice: Subject to any disclaimer, the term of this patent is extended or adjusted under 35 U.S.C. 154(b) by 0 days.

(21) Appl. No.: 14/857,301

(22) Filed: Sep. 17, 2015

(65) Prior Publication Data

US 2016/0083360 A1 Mar. 24, 2016

(30) Foreign Application Priority Data

Sep. 18, 2014 (TW) .............................. 103132305 A

(51) Int. Cl.
*C07D 301/12* (2006.01)
(52) U.S. Cl.
CPC .................................. *C07D 301/12* (2013.01)
(58) Field of Classification Search
CPC .................................................. C07D 301/12
USPC ........................................................ 549/531
See application file for complete search history.

(56) References Cited

U.S. PATENT DOCUMENTS

| 2,716,123 | A | 8/1955 | Frostick et al. |
| 3,275,661 | A | 9/1966 | Widmer et al. |
| 8,697,895 | B2 | 4/2014 | Crampton et al. |
| 2003/0055293 | A1* | 3/2003 | Wurziger ............ B01J 19/0093 568/451 |
| 2008/0045729 | A1 | 2/2008 | Takai et al. |
| 2013/0302216 | A1* | 11/2013 | Carlberg ............ B01D 11/0488 422/187 |

FOREIGN PATENT DOCUMENTS

| EP | 2462130 B1 | 7/2013 |
| GB | 735974 A | 8/1955 |
| JP | 2006-188476 A | 7/2006 |
| JP | 2009-256217 A | 11/2009 |
| JP | 2009-263240 A | 11/2009 |
| JP | 5163921 B2 | 3/2013 |
| WO | 0183466 A1 | 11/2001 |

OTHER PUBLICATIONS

Campanella et al., "Degradation of the oxirane ring of epoxidized vegetable oils in liquid-liquid heterogeneous reaction systems", Chemical Engineering Journal 118 (2006) 141-152.
Campanella et al., "Degradation of the oxirane ring of epoxidized vegetable oils in liquid-liquid systems: II. Reactivity with solvated acetic and peracetic acids", Latin American Applied Research (2005) 35:211-216.
Gisdakis et al., "Olefin epoxidation by dioxiranes and percarboxylic acids: an analysis of activation energies calculated by a density functional method", Journal of Physical Organic Chemistry, 2001; 14:328-332.
Gisdakis et al., "Solvent effects on the activation barriers of olefin epoxidation—a density functional study", Eur. J. Org. Chem., 2001, 719-723.
Hildebrand, Joel H., "Solubility", American Chemical Society, 1916, 38, 1452-1473.
Murray et al., "Dioxirane Chemistry. Part 23. The Effect of Solvent on the Dimethyldioxirane Epoxidation Reaction", J. Chem. Soc. Perkin Trans. 2, 1993, pp. 2203-2207.
Sapunov et al., "Solvent effect in the Prilezhaev reaction", SciFinder, Izvestiga Vysshikh Uchebnykh Zavedenii, Khimiya i Khimicheskaya Tekhnologiya, vol. 8, Issue 5, pp. 771-775, Journal, 1965, Coden: Ivukar, SSN: 0579-2991 (providing English Abstract only.).
Shi et al., "Mechanism on epoxidation of alkenes by peracids: A protonation-promoted pathway and its quantum chemical elucidation", Journal of Molecular Catalysis A: Chemical 238 (2005) 13-25.
Ullmann's Encyclopedia of Industrial Chemistry, Chapter Epoxide, Wiley-VCH, 2000, pp. 139-154.
Ullmann's Encyclopedia of Industrial Chemistry, vol. 26, A Chapter "Peroxy Compounds, Organic", 2012, pp. 325-360.

* cited by examiner

Primary Examiner — T. Victor Oh
(74) Attorney, Agent, or Firm — Lerner, David, Littenberg, Krumholz & Mentlik, LLP

(57) ABSTRACT

The subject invention is related to a process for the epoxidation of olefin with peroxide, comprising reacting peroxide with olefin in the presence a solvent, wherein the solvent has Hansen Solubility Parameters (HSPs) of $\delta_{T,solvent}$ and $\delta_{H,solvent}$ and the epoxide product has Hansen Solubility Parameters (HSPs) of $\delta_{T,product}$ and $\delta_{H,product}$, and wherein:

$\delta_{T,product} - 6 \leq \delta_{T,solvent} \leq \delta_{T,product} + 6$, and $\delta_{H,product} - 6 \leq \delta_{H,solvent}$.

15 Claims, No Drawings

PROCESS FOR THE EPOXIDATION OF OLEFINS

CROSS-REFERENCE TO RELATED APPLICATIONS

The present application claims priority from Taiwanese Application No. 103132305 filed Sep. 18, 2014, the disclosure of which is hereby incorporated herein by reference.

BACKGROUND OF THE INVENTION

Field of the Invention

The subject invention is related to a process for the epoxidation of olefin with peroxide, particularly related to a process for epoxidation in a flow reactor which may increase the selectivity of epoxidation of olefin.

Description of the Related Art

There are many methods for the epoxidation of olefin, for example, Ullmann's Encyclopedia of Industrial Chemistry (Chapter: Epoxide, Wiley-VCH, 2000) discloses that epoxidation of olefin can be carried out with peroxy acid, hydrogen peroxide, halogenated alcohol or molecular oxygen. Dienes are commonly epoxidized with peroxy acid, such as peracetic acid. U.S. Pat. No. 2,716,123 A (1955, UCC) discloses a process in which diene was added dropwise with a 25.5% peracetic acid in acetone solution at a temperature of 20 to 40° C. over a period of 2 to 3 hours for a reaction over 11 to 16 hours, through which the cycloaliphatic esters of Formula 1, Formula 3, Formula 5, Formula 7 and Formula 9 can be epoxidized into the cycloaliphatic diepoxy compounds of Formula 2, Formula 4, Formula 6, Formula 8 and Formula 10 with yields of 85.5%, 84%, 85.4%, 95% and 79%, respectively.

Formula 1

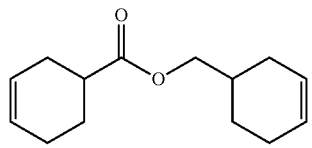

Formula 2

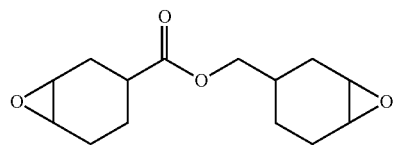

Formula 3

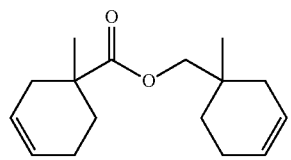

Formula 4

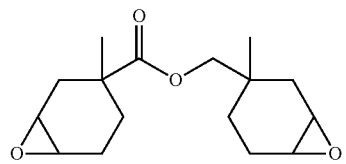

Formula 5

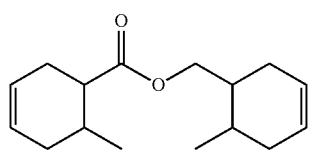 [SMILES: CC1CC=CCC1COC(=O)C1CC=CCC1C]

Formula 6

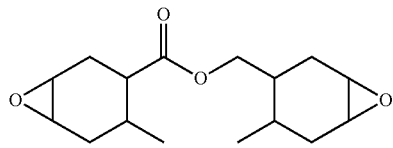

Formula 7

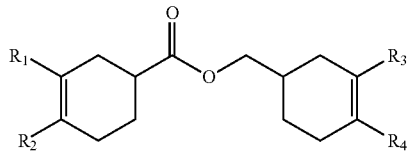

$R_1 = Me/H, R_2 = Me/H, R_3 = Me/H, R_4 = Me/H$

Formula 8

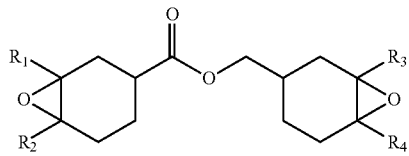

$R_1 = Me/H, R_2 = Me/H, R_3 = Me/H, R_4 = Me/H$

Formula 9

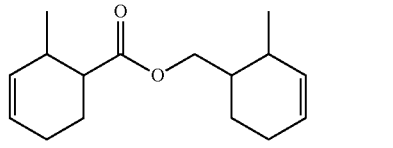 [SMILES: CC1C=CCCC1COC(=O)C1CCC=CC1C]

Formula 10

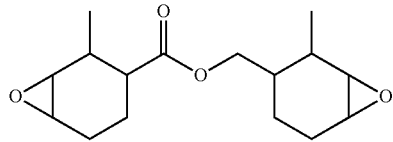

GB 735974 A (1955, UCC) discloses epoxidizing Formula 11 into Formula 12 with peracetic acid obtained by oxidation of acetaldehyde. U.S. Pat. No. 3,275,661 A (1966, Ciba) discloses adding a 42% peracetic acid over 1 hour at a temperature of 30° C. into benzene solution containing the diene compound of Formula 13 and sodium acetate, and maintaining the reaction under 30° C. for 4 hours to produce the diepoxide of Formula 14. JP 2006-188476 A (2006, Daicel) discloses a process for producing high-purity cycloaliphatic diepoxide in which peracetic acid with a water content of 0.8 wt. % or less is added at 30° C. for a reaction for 3 hours, and which can epoxidize the cycloaliphatic diolefinic compound of Formula 15 to the cycloaliphatic diepoxide of Formula 16.

Formula 11

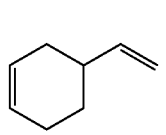

Formula 12

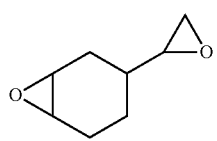

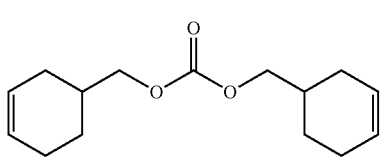 [SMILES: O=C(OCC1CC=CCC1)OCC1CC=CCC1]
Formula 13

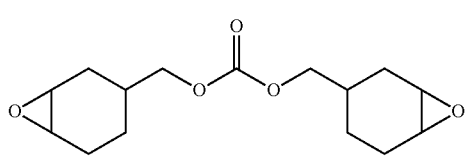
Formula 14

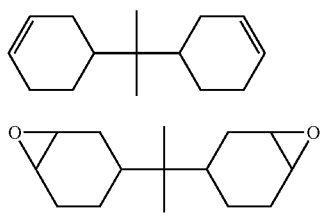
Formula 15

Formula 16

U.S. Pat. No. 8,697,895 B2 (2014, DOW) discloses epoxidation of propene, using a titanium silicalite-1 (TS-1) catalyst, methanol as solvent with a non-reactive co-solvent, wherein the co-solvent has a solubility dispersion force parameter $\delta_D$ of 0.4 to 1.0, a polar force parameter $\delta_p$ of 0.0 to 0.5, and a hydrogen bonding force parameter $\delta_H$ of 0.0 to 0.3. Use of co-solvent can reduce the amount of methanol solvent used, and further reduce alcoholysis. Furthermore, since the co-solvent can be separated from the aqueous layer by decanting and most of the by products are dissolved in the aqueous layer, the organic layer may be returned to reaction without byproduct accumulation, allowing a simplified recycling procedure. Another advantage is that the epoxidized product can enter the organic phase of the co-solvent and thus allows a reduced plugging of the catalyst pores to increase catalyst lifetime. EP 2462130 B1 (2013, DOW) also discloses epoxidation of propene with TS-1 catalyst, methanol solvent and non-reactive co-solvent(s) having solubility parameters similar to propylene oxide, which can reduce the amount of methanol solvent required, reduce alcoholysis by-products, increase selectivity of epoxidized products, increase catalyst lifetime and allow a simplified recycling procedure.

In a conventional batch reaction for epoxidation of olefin with peroxides, addition of peroxides should be controlled at a lower temperature and for a long time; in this case, a bigger reactor takes more time and the temperature is harder to control, which can raise safety concerns. PCT/EP2001/003875, JP 5163921 B2, JP 2009-256217 A, JP 2009-263240 A disclose processes for the epoxidation of olefins with a micro-reactor, which is safer and allows continuous production; among them, JP 2009-263240 A discloses oxidizing acetaldehyde with oxygen and cobalt catalyst in a micro-reactor, obtaining 40% peracetic acid through distillation, and then, in a stainless steel tube with 0.26 mm inner diameter, epoxidizing the aliphatic diolefinic compound of formula (1) into the aliphatic diepoxide of formula (2) with a yield of 79%.

For epoxidation of olefin with peroxides, in order to suppress side reactions of hydrolyzing the epoxides, the reaction should be carried out at a lower temperature and for a long time; however, this imposes a significant limitation on production capacity. By epoxidizing vegetable oil with peracetic acid, Campanella, A. and Baltanás, M. A. conducted further studies on hydrolysis (Chemical Engineering Journal 2006, 118, 141-152; Latin American Applied Research 2005, 35, 211-216 and 205-210), and found that peracetic acid, carboxylic acid, proton acid, water and hydrogen peroxide will cause hydrolyzation. Since most hydrolyzing reactions are related to proton acid, it is common to add a buffer agent such as acetate salts or phosphate salts to the reaction for controlling pH value, or use anhydrous peracetic acid obtained through acetaldehyde oxidation process to avoid hydrolyzation of epoxides caused by proton acid, water and hydrogen peroxide. However, it is still not possible to avoid hydrolyzation of epoxides caused by peracetic acid and carboxylic acid.

For epoxidation of olefin with peroxides, it is difficult to simultaneously improve both conversion rate and selectivity. Especially for epoxidation of diolefin, at a high conversion rate, though monoepoxide in the products is reduced, hydrolysate selectivity is higher; conversely, at low hydrolysate selectivity (e.g. at low temperature or low reactant concentration), higher monoepoxide selectivity is found.

SUMMARY OF THE INVENTION

The inventors of the subject invention have successfully developed a process for epoxidation of olefin with a low degree of hydrolyzation and high selectivity, in particular, a process for manufacturing cycloaliphatic diepoxide. The process epoxidizes olefins with peroxide by using a suitable solvent based on its solubility parameter.

The subject invention is related to a process for the epoxidation of olefin, comprising reacting peroxide with the olefin in a reactor in the presence a solvent, wherein the solvent has solubility parameters of $\delta_{T,solvent}$ and $\delta_{H,solvent}$, and an epoxide product has solubility parameters of $\delta_{T,product}$ and $\delta_{H,product}$, and wherein: $\delta_{T,product}-6 \leq \delta_{T,solvent} \leq \delta_{T,product}+6$, and $\delta_{H,product}-6 \leq \delta_{H,solvent}$.

DETAINED DESCRIPTION OF THE INVENTION

Selecting solvent based on solubility parameters is a commonly used technique for a polymer composition, such as a coating composition, for processing and modification of polymers, elastomer industry and selection of additives. The idea of solubility parameter was first developed by Hildebrand J. H. (J. Am. Chem. Soc. 1916, 38,1452-1473), who considered that the square root of the cohesive energy density of a substance can represent the intensity of the interaction between liquid molecules. Based on above concept, Hansen C. M. developed in his Ph.D thesis in 1967 a three-dimensioned solubility parameter system, known as Hansen Solubility Parameters (HSPs). HSP comprises three dimensions: $\delta_D$, $\delta_P$, and $\delta_H$, which are respectively referred to as dispersion force, polarity and hydrogen bond, and the sum of the squares of these diamensions is equal to $\delta^2_T$, i.e. $\delta_T=(\delta^2_D+\delta^2_P+\delta^2_H)^{1/2}$. Calculation of the solubility parameters is based on group-contribution method, which is detailed in Hansen, Charles M. 2007, *Hansen solubility parameters: a user's handbook*, Boca Raton, Fla.: CRC Press and Krevelen, D. W. van; Hoftyzer, P. J. 1976. *Properties of Polymers: Their Estimation and Correlation with Chemical Structure;* 2nd ed.; Elsevier: Amsterdam; New York.

To study the effect of a solvent in epoxidation, Sapunov and Lebedev (Izvestiya Vysshikh Uchebnykh Zavedenii, Khimiya i Khimicheskaya Tekhnologiya 1965, 8, 771-775) performed epoxidation of olefin with peracetic acid, and found that higher basicity of the solvent will cause a smaller reaction rate constant for epoxidation. Murray and Gu (J. Chem. Soc., Perkin Trans. 2 1993, 2203-2207) performed epoxidation of trans-ethyl cinnamate and cyclohexene with dioxirane, and found that a stronger hydrogen bond of a solvent will cause a faster reaction rate of epoxidation with dioxirane. Gisdakis and Rösch (Eur. J. Org. Chem. 2001, 719-723; J. Phys. Org. Chem. 2001, 14, 328-332.) and Shi et al. (J. Mol. Catal. A: Chem. 2005, 238, 13-25.) conducted computational simulations for the reaction mechanism of epoxidation of olefin with peroxy acids, and found that the proton acid in the reaction system or hydrogen bond of the solvent can lower the potential energy of the transition state during epoxidation, and thus can further increase the reaction rate for epoxidation of olefin. However, none of the above studies provide a solution for the decrease in the amount of monomers during diene epoxidation and the amount of hydrolysis.

Based on massive computational simulations and experiments, the inventors of the subject invention found that, for epoxidation of olefin with peroxide, an increased selectivity for the epoxide products and a decreased selectivity for hydrolyzation can be obtained by using a solvent having a solubility parameter $\delta_{T,solvent}$ equal to or in the range of a total solubility parameter of the epoxide product, $\delta_{T,product}$, ±6 (i.e. $\delta_{T,product}-6 \leq \delta_{T,solvent} \leq \delta_{T,product}+6$) and a hydrogen bond solubility parameter $\delta_{H,solvent}$ equal to or higher than a solubility parameter of the epoxide product, $\delta_{H,product}$, −6 (i.e. $\delta_{H,product}-6 \leq \delta_{H,solvent}$), preferably, the solvent having a solubility parameter $\delta_{T,solvent}$ equal to or in the range from $\delta_{T,product}-6$ to $\delta_{T,product}+3$ (i.e. $\delta_{T,product}-6 \leq \delta_{T,solvent} \leq \delta_{T,product}+3$) and a solubility parameter $\delta_{H,solvent}$ equal to or higher than $\delta_{H,product}-6$ (i.e. $\delta_{H,product}-6 \leq \delta_{H,solvent}$).

It should be understood that all the value ranges referred to in this application cover every sub-range thereof. For example, "$\delta_{T,product}-6$ to $\delta_{T,product}+3$" includes every sub-range between the minimum value $\delta_{T,product}-6$ and maximum value $\delta_{T,product}+3$ (such as $\delta_{T,product}-5.2$ to $\delta_{T,product}+1.5$ and $\delta_{T,product}-3.5$ to $\delta_{T,product}+0.8$) and said minimum value and maximum value, i.e. covering a range between a minimum value equal to or higher than $\delta_{T,product}-6$ and a maximum value equal to or lower than $\delta_{T,product}+3$. Since the disclosed value ranges are continuous, they cover every single value between the minimum value and maximum value. Unless otherwise specified, all of the value ranges referred to in this application are approximate values.

The species of the solvent used in the epoxidation process of the subject invention may vary based on the species of the olefin and reaction conditions. Suitable solvents include aliphatic carboxylic acid esters, alcohols or the alkyl-substituted, or cyclic or aryl-substituted derivatives thereof, hydrocarbons or the alkyl-substituted or halogen-substituted derivatives thereof, ketones or the alkyl-substituted derivatives thereof, nitriles or the aryl-substituted derivatives thereof, ethers, heterocyclic compounds, or the mixture of one or more of the above-mentioned substances. For example, suitable solvents include aliphatic carboxylic acid esters such as methyl acetate, ethyl acetate, propyl acetate and butyl acetate; alcohols in straight or branched forms or the alkyl-substituted derivatives thereof, such as methanol, ethanol, propanol, butanol, pentanol, hexanol, heptanol and octanol; cyclic or aryl-substituted derivatives of alcohols such as cyclohexanol and benzyl alcohol; hydrocarbons in straight or branched forms or the alkyl-substituted derivatives thereof such as hexane and octane; cycloaliphatic hydrocarbons or the alkyl-substituted derivatives thereof such as cyclohexane and cycloheptane; aromatic hydrocarbons or the alkyl-substituted aromatic hydrocarbons thereof such as benzene, naphthalene, toluene and xylene; chlorinated hydrocarbons such as chloroform, chlorobenzene and dichlorobenzene; ketones or the derivatives thereof such as acetone, butanone and methyl isobutyl ketone; nitriles or the derivatives thereof such as acetonitrile, propionitrile, butyronitrile and benzeneacetonitrile; ethers or the derivatives thereof such as ethyl ether and butyl ether; heterocyclic compounds such as dioxane and tetrahydrofuran. In order to solubilize peroxide used as an epoxidizing agent, and in view of the solubility of the olefin reactant and the selectivity of the epoxide product, preferred solvents include acetonitrile, acetone, N-butanol, 2-butanol, iso-octanol, cyclohexanol, benzyl alcohol, methyl acetate, ethyl acetate, butyl acetate, chloroform, dioxane and tetrahydrofuran, and such solvents may be used solely or in combination.

The reactor of the subject invention is not limited to any type of reactor. In an embodiment of the subject invention, the reactor is a micro-reactor. In another embodiment of the subject invention, the reactor can be either a batch reactor or a continuous reactor, wherein the continuous reactor may be a flow reactor.

The flow reactor may be a commercially available model, such as Advanced-Flow® Reactor from Corning Inc.; Modular MicroReaction System, Lonza FlowPlate®, ART® plate reactors and Miprowa® from Ehrfeld Mikrotechnik BTS GmbH; Qmix® microreaction system from Cetoni; LABTRIX® START, LABTRIX® S1, KILOFLOW® and PLANTRIX® from Chemtrix; HTM®, MR-LAB®, MR PILOT® and XXL® SERIES from Little Things Factory; Asia® Flow Chemistry System from Syrris; KeyChem®, CYTOS-200® and CYTOS-2000® from YMC. Moreover, the subject invention may use any self-made flow reactor. The inner diameter of the flow reactor is not limited to any specific value. Normally, the inner diameter ranges from 0.01 mm to 10 mm, preferably from 0.05 mm to 8 mm; in view of the manufacturability, efficiency, and production capacity of the reactor, the most preferred inner diameter ranges from 0 1 mm to 5 mm. The flow reactor may have a single passage, parallel passages or serial passages.

The subject invention is related to a process for epoxidation of olefin with peroxide, and the peroxide acts as an epoxidizing agent. The peroxide may include peroxy acids, hydroxyphenyl peracids, alkyl hydroperoxides, alkyl-substituted phenyl hydroperoxides, ester group-substituted phenyl hydroperoxides and heterocyclic hydroperoxides. Suitable peroxide includes hydrogen peroxide, performic acid, peracetic acid, tert-butyl peroxide, di(tert-butyl)peroxide, tert-amyl hydroperoxide, cumene hydroperoxide, isobutylbenzene hydroperoxide, benzoyl peroxide, cyclohexanone peroxide, dicumyl peroxide, methyl cyclohexyl hydroperoxide, tetralin hydroperoxide, ethylnaphthalene hydroperoxide and benzoyl tert-butyl peroxide. In addition, in view of industrial availability, the peroxide may be peracetic acid, tert-butyl peroxide and cumene hydroperoxide.

The amount of the peroxide, which acts as an epoxidizing agent, is not limited, and is preferably determined based on the amount of the olefins Normally, the equivalence ratio of the peroxide, with respect to the olefins, is 0.5 to 3, preferably 0.8 to 2.8, and most preferably 1 to 2.6. In the case where a flow reactor is used, the amount of the peroxide may also be determined based on the volume ratio or flow velocity ratio of two components in the reactor; typically, the flow velocity ratio of the peroxide to the olefin is from 0.2 to 5, preferably from 0.5 to 4, and most preferably from 0.8 to 3.

The peroxide of the subject invention may be either commercially available or self-made peroxide. For self-made peroxide, the preparation thereof is not specifically limited; as disclosed in Ullmann's Encyclopedia of Industrial Chemistry (Vol. 26, Chapter: Peroxy Compounds, Organic, Wiley-VCH, 2012), the peroxide may be obtained by oxidizing corresponding carboxylic acids, aldehydes, alcohols, esters and alkenes. The concentration of the peroxide in the peroxide solution is not specifically limited, and may be from 20 to 70 wt. %, preferably 20 to 65 wt. %, and most preferably 25 to 60 wt. %. In the case where the amount of peroxide in the solution is less than 20 wt. %, the conversion rate is drastically decreased due to the insignificant amount of peroxide. Where the amount of peroxide in the solution is greater than 70 wt. %, the process will be unsuitable for industrial manufacturing and raise safety concerns.

Buffering solvent may be added during the reaction. The buffering solvent used in the subject invention is not specifically limited, and may be acetate salts or phosphate salts. Suitable buffering solvent includes sodium acetate, sodium dihydrogen phosphate and sodium hydrogen phosphate, in which the conjugated metal ions may be replaced with other alkaline metal ions or alkaline earth metal ions to form other acetate salts or phosphate salts such as potassium acetate, potassium dihydrogen phosphate and potassium hydrogen phosphate. The amount of the buffering solvent is not greater than 5 wt. %, preferably not greater than 2 wt. % in the solution.

The subject invention is related to epoxidation of olefin, and the process of the subject invention may be applied to any type of olefin compound. The olefin compound comprises at least one double bond, and may comprise two or more double bonds. Such double bond may be located inside or at a terminal of the molecule structure. The olefin compound may be a cyclic compound such as cyclohexene, 4-ethenyl-1-cyclohexene, 1-methyl-5-(1-methylvinyl)cyclohexene, dicyclopentadiene, bicyclohexyl-3,3'-diene, 4-(cyclohex-3-en-1-yl-methyl)cyclohexene, 2,2-bis(3',4'-cyclohexenyl)propane, 2,2-bis(cyclohexen-3-yl)propane, and the derivatives or mixture thereof.

The olefin compound is preferably a cycloaliphatic or aromatic compound, such as 3-cyclohexene-1-carboxylic acid, 3-cyclohexen-1-yl methyl ester; 3-cyclohexene-1-carboxylic acid, 6-methyl-, (6-methyl-3-cyclohexen-1-yl) methyl ester; 3-cyclohexene-1-carboxylic acid, 3-methyl-(3-methyl-3-cyclohexen-1-yl)methyl ester; 3-cyclohexene-1-carboxylic acid, 4-methyl-, (4-methyl-3-cyclohexen-1-yl) methyl ester; 3-cyclohexene-1-carboxylic acid, 1-methyl-, (1-methyl-3-cyclohexen-1-yl)methyl ester; 3-cyclohexene-1-carboxylic acid, 2-methyl-, (2-methyl-3-cyclohexen-1-yl) methyl ester; 3-cyclohexene-1-carboxylic acid, 3,4-dimethyl-, (3,4-dimethyl-3-cyclohexen-1-yl)methyl ester; 3-cyclohexene-1-carboxylic acid, 1-(3-cyclohexen-1-yl) ethyl ester; 3-cyclohexene-1-carboxylic acid, 1-(3-cyclohexen-1-yl)-1-methylethyl ester; bicyclo [2.2.1]hept-5-ene-2-carboxylic acid, 3-methyl-, (3-methylbicyclo[2.2.1]hept-5-en-2-yl)methyl ester; 5-norbornene-2-carboxylic acid, ethylene ester; 1,6-hexanediol bis(norborn-2-ene-5-carboxylate); 3-cyclohexene-1-carboxylic acid, ethylene ester; 3-cyclohexene-1-carboxylic acid, 4-methyl-, 1,2-ethanediyl ester; 3-cyclohexene-1-carboxylic acid, 4-methyl-, 1-methyl-1,2-ethanediyl ester; 3-cyclohexene-1-carboxylic acid, 6-methyl-, 1,1'-(1,6-hexanediyl)ester; 3-cyclohexene-1-carboxylic acid, 1,1'-[1,4-cyclohexanediylbis(methylene)] ester; carbonic acid, C,C'-[1,4-cyclohexanediylbis(methylene)] C,C'-bis(3-cyclohexen-1-ylmethyl)ester; ethanedioic acid, 1,2-bis(3-cyclohexen-1-ylmethyl)ester; hexanedioic acid, 1,6-bis(3-cyclohexen-1-ylmethyl)ester; maleic acid, bis(6-methyl-3-cyclohexen-1-ylmethyl)ester; 1,4-cyclohexanedicarboxylic acid, 1,4-bis(3-cyclohexen-1-ylmethyl) ester; 1,1,2,2-ethanetetracarboxylic acid, tetrakis(3-cyclohexen-1-ylmethyl)ester; 1,2,3,4-butanetetracarboxylic acid, tetrakis(3-cyclohexen-1-ylmethyl)ester; bicyclo [2.2.1]hept-5-ene-2-carboxylic acid, 2,2'-[2,2-bis[[(bicyclo [2.2.1]hept-5-en-2-ylcarbonyl)oxy]methyl]-1,3-propanediyl]ester; bicyclo [2.2.1]hept-5-ene-2-carboxylic acid, 2,2'-[2-[[(bicyclo [2.2.1]hept-5-en-2-ylcarbonyl)oxy]methyl]-2-ethyl-1,3-propanediyl]ester; di(cyclohex-3-enylmethyl)carbonate; di[1-(3-cyclohexenyl)ethy]carbonate; diallyl 1,2-cyclohexanedicarboxylate; diallyl tetrahydrophthalate; 1,2-cyclohexanedicarboxylic acid, 1,2-bis(3-cyclohexen-1-ylmethyl)ester; 4-cyclohexene-1,2-dicarboxylic acid, 1,2-bis(3-cyclohexen-1-ylmethyl)ester; poly[oxy(1-oxo-1,6-hexanediyl)], α-(3-cyclohexen-1-ylmethyl)-ω-[(3-cyclohexen-1-ylcarbonyl)oxy]-; and the derivatives or mixture thereof.

The olefin compound may also be a compound having an ether bond in its structure, such as bis(cyclopent-2-enyl) ether; bis(cyclopent-3-enyl)ether; 4-(cyclohex-3-en-1-yl-methoxymethyl)cyclohexene; cyclohexene, 3,3'[methylenebis(oxy)]bis-; 4-(cyclohex-3-en-1-yloxymethoxy) cyclohexene; ethyleneglycol bis(2-cyclohexenyl)ether; isopropylene glycol bis(2-cyclohexenyl)ether; bis(3-cyclohexen-1-ylmethyloxy)methane; methane, bis(5-norbornen-2-ylmethoxy)-; bicyclo[2.2.1]hept-2-ene, 5,6-bis[(2-propen-1-yloxy)methyl]-; bisphenol A diallyl ether; bisphenol F diallyl ether; cyclohexene, 4,4-bis[(2-cyclohexen-1-yloxy) methyl]-; tetraallyl pentaerythritol ether; and the derivatives or mixture thereof.

The olefin compound may also be a compound having heterocycle or amino group in its structure, such as 3-cyclohex-2-en-1-yl-2,4-dioxaspiro[5.5]undec-9-ene; spiro[m-dioxane-5,2'-[5]norbornene], 2-(5-norbomen-2-yl)-; bis[4-(diallylamino)phenyl]methane; benzenamine, N,N-di-2-propenyl-4-(2-propenyloxy)-; and the derivatives or mixture thereof. The olefin compound may also be a compound having silicate or phosphate in its structure, such as Cyclohexene, 4,4',4''-[(methylsilylidyne)tris(oxymethylene)]tris-; Silane, tris(bicyclo [2.2.1]hept-5-en-2-ylmethoxy)methyl-; Tri(cyclohex-3-enylmethoxy)phenyl silane; Silicic acid ($H_4SiO_4$), tetrakis(3-cyclohexen-1-ylmethyl)ester; 3-Cyclohexene-1-methanol, 1,1',1''-phosphate; 1,3,5-Triallylisocyanurate; and the derivatives or mixture thereof.

In an embodiment of the subject invention, the olefin compound is selected from the compounds listed in the following table:

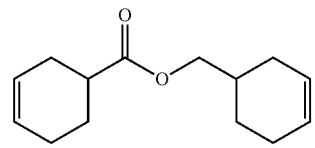

3-cyclohexene-1-carboxylic
acid, 3-cyclohexen-1-ylmethyl
ester

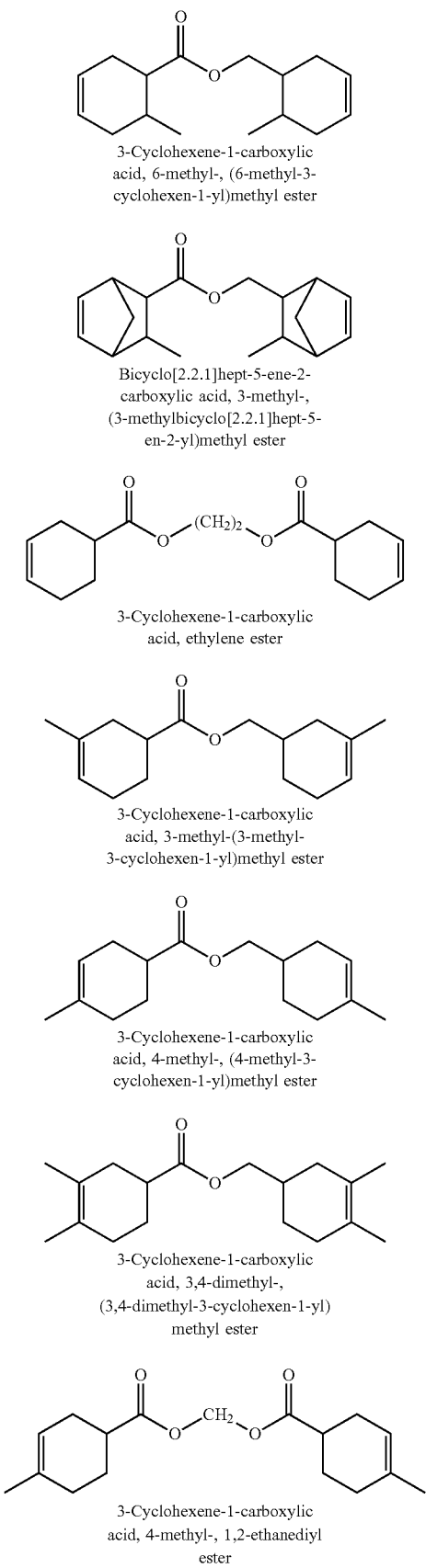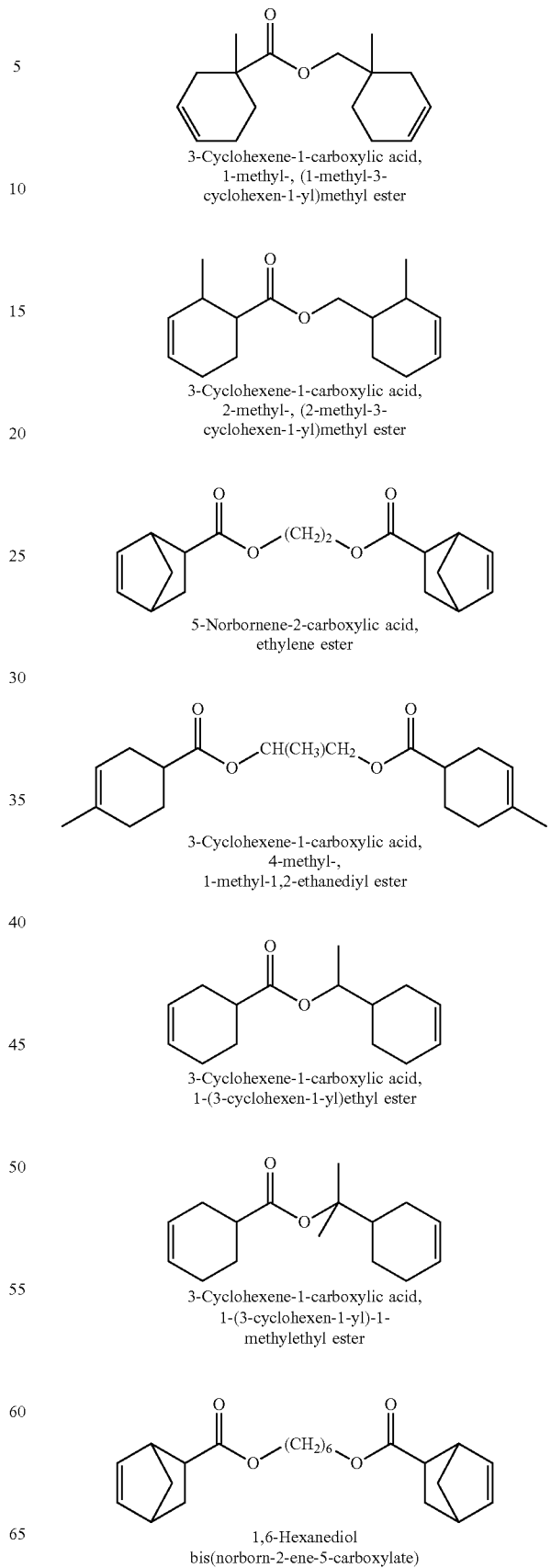

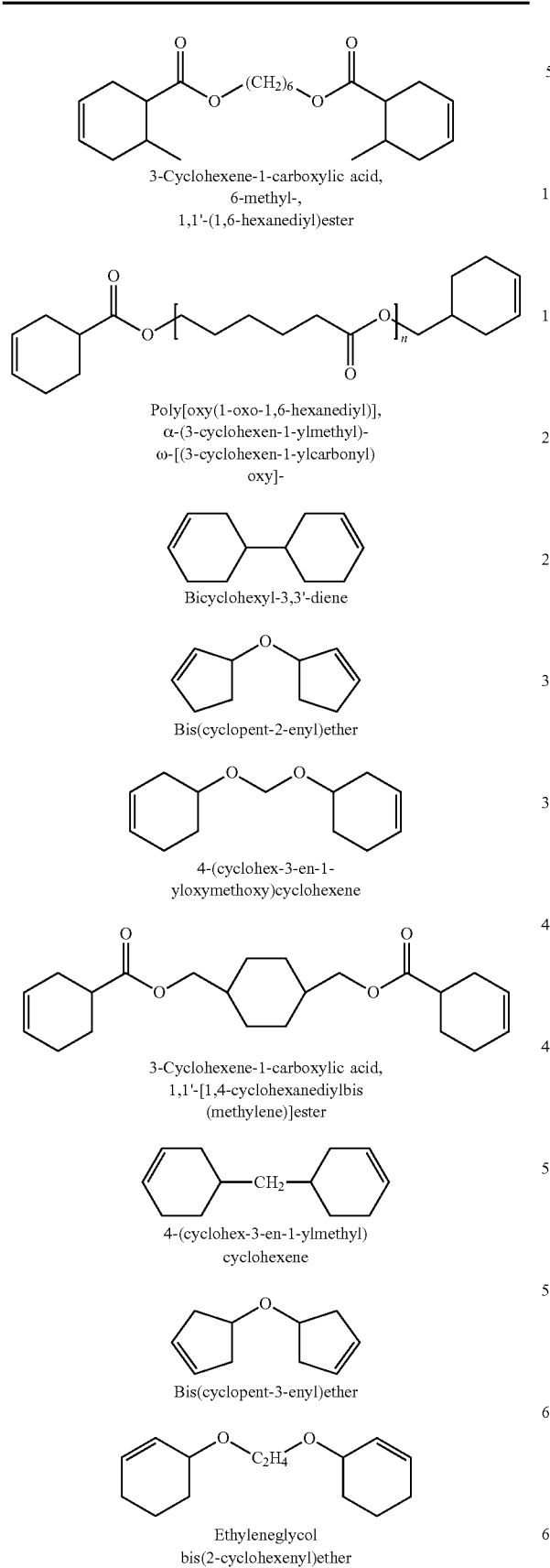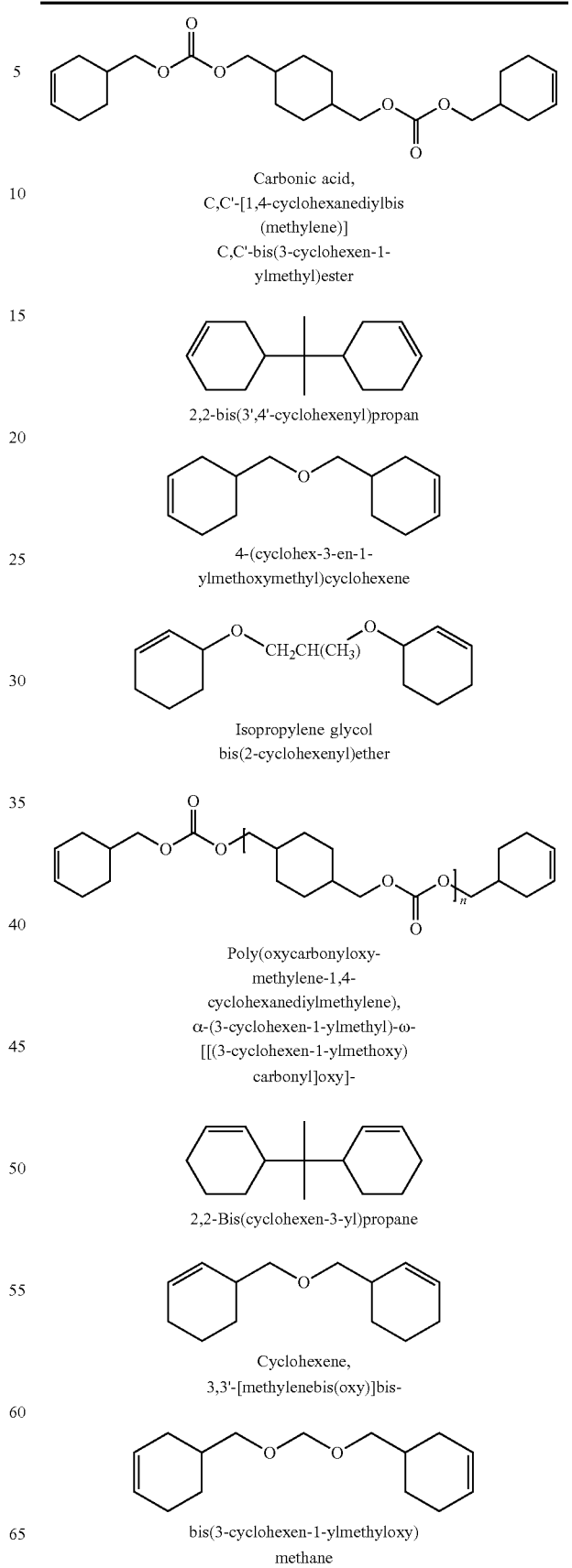

-continued

Diallyl 1,2-cyclohexanedicarboxylate 1,2-Cyclohexanedicarboxylic acid, 1,2-bis(3-cyclohexen-1-ylmethyl)ester Cyclohexene Methane, bis(5-norbornen-2-ylmethoxy)-

Diallyl tetrahydrophthalate

4-Cyclohexene-1,2-dicarboxylic acid, 1,2-bis(3-cyclohexen-1-ylmethyl)ester 4-ethenylcyclohexene Di(cyclohex-3-enylmethyl) carbonate -continued Bicyclo[2.2.1]hept-2-ene, 5,6-bis[(2-propen-1-yloxy)methyl]-

Bis[4-(diallylamino)phenyl]methane

1-Methyl-5-(1-methylvinyl)cyclohexene

Di[1-(3-cyclohexenyl)ethy] Carbonate

Bicyclo[2.2.1]hept-5-ene-2,3-dicarboxylic acid, 2,3-bis[2-[(3a,4,5,6,7,7a-hexahydro-4,7-methano-1H-inden-5-yl)oxy]ethyl]ester, Benzenamine, N,N-di-2-propenyl-4-(2-propenyloxy)-

Dicyclopentadiene

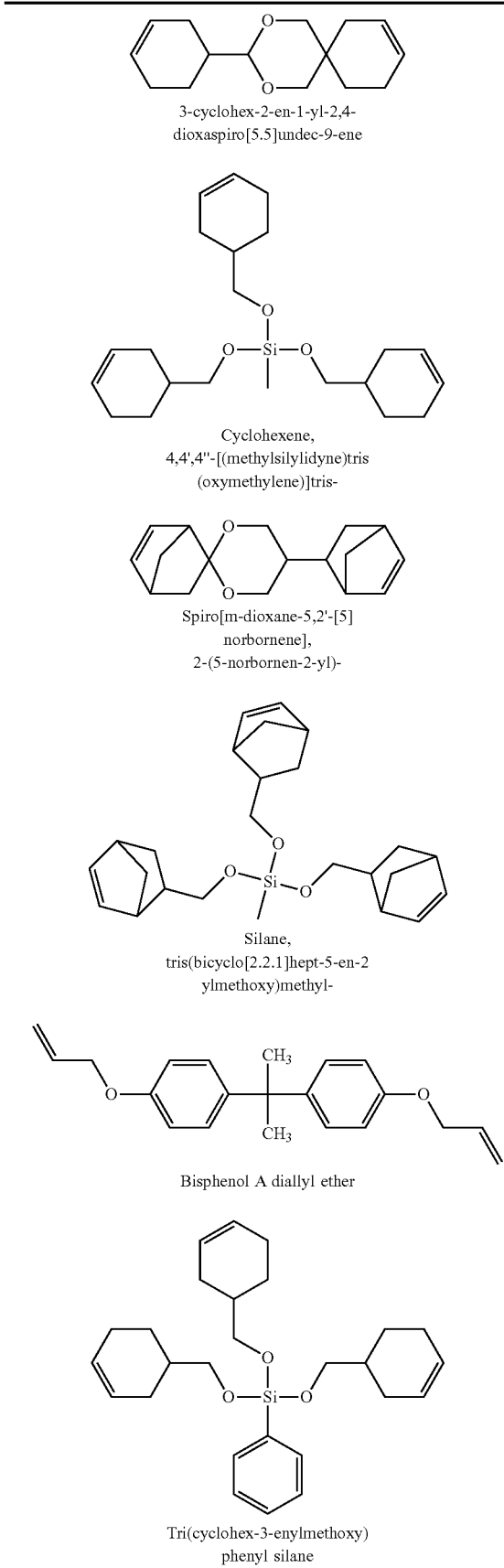
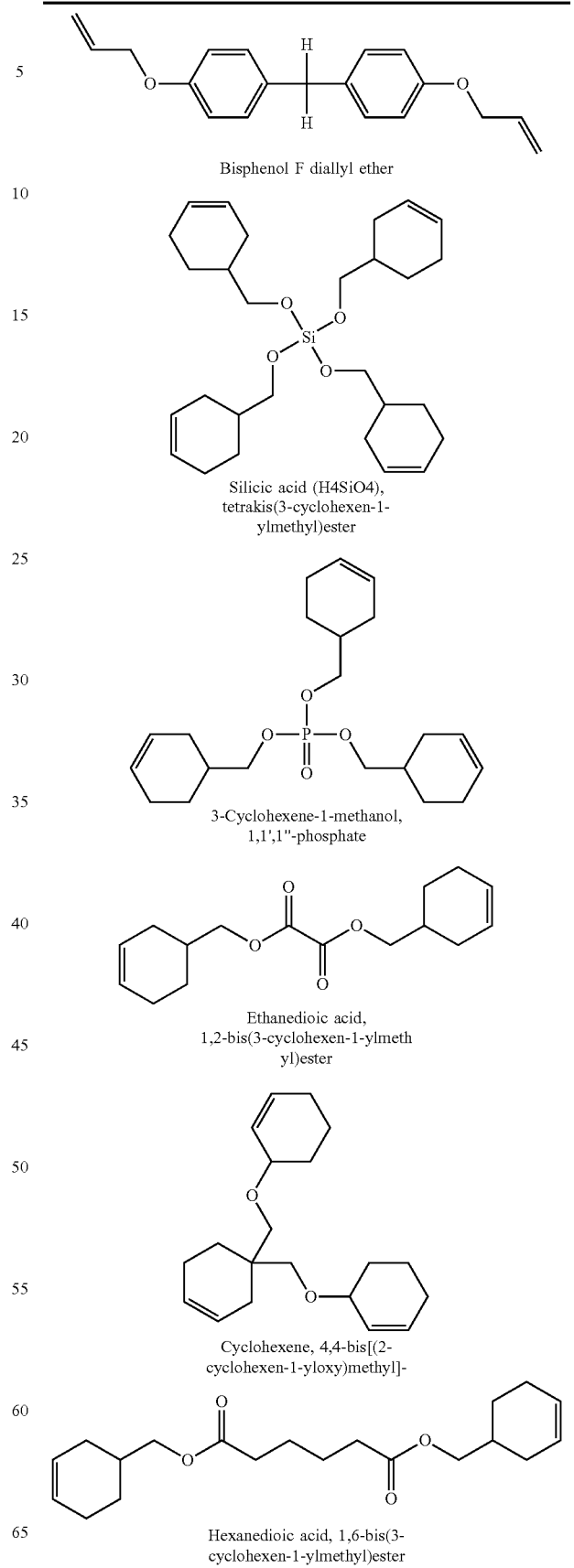

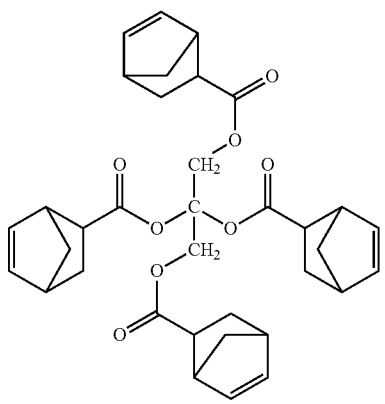 [SMILES: O=C(OCC(COC(=O)C1CC2C=CC1C2)(OC(=O)C1CC2C=CC1C2)OC(=O)C1CC2C=CC1C2)C1CC2C=CC1C2]

Bicyclo[2.2.1]hept-5-ene-2-
carboxylic acid,
2,2'-[2,2-bis[[(bicyclo[2.2.1]hept-
5-en-2-ylcarbonyl)oxy]methyl]-
1,3-propanediyl]ester

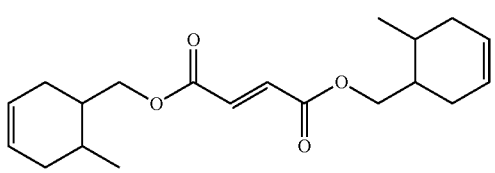 [SMILES: CC1CC=CCC1COC(=O)/C=C/C(=O)OCC1CC=CCC1C]

Maleic acid, bis(6-methyl-3-
cyclohexen-1-ylmethyl)ester

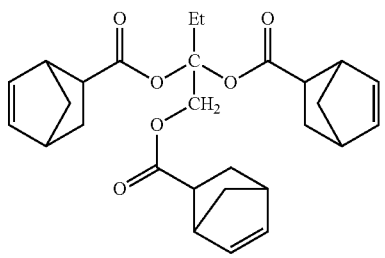 [SMILES: CCC(COC(=O)C1CC2C=CC1C2)(OC(=O)C1CC2C=CC1C2)OC(=O)C1CC2C=CC1C2]

Bicyclo[2.2.1]hept-5-ene-2-
carboxylic acid,
2,2'-[2-[[(bicyclo[2.2.1]hept-5-
en-2-ylcarbonyl)oxy]methyl]-2-
ethyl-1,3-propanediyl]ester

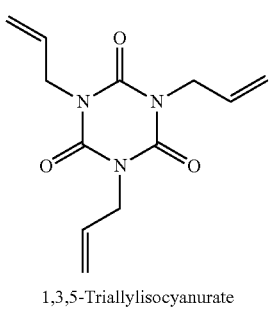

1,3,5-Triallylisocyanurate

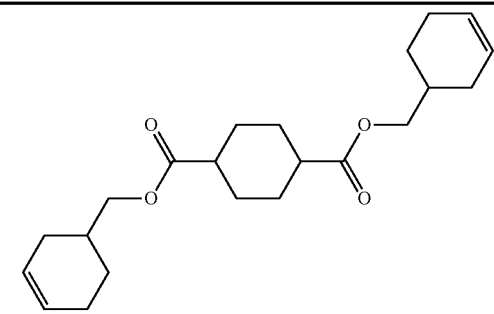

1,4-Cyclohexanedicarboxylic acid,
1,4-bis(3-cyclohexen-1-ylmeth
yl)ester

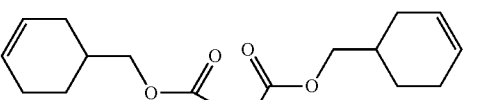

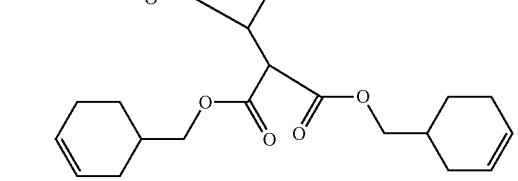

1,1,2,2-Ethanetetracarboxylic acid,
tetrakis(3-cyclohexen-1-
ylmethyl)ester

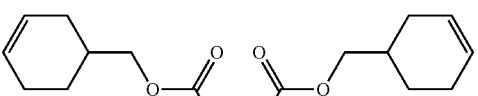

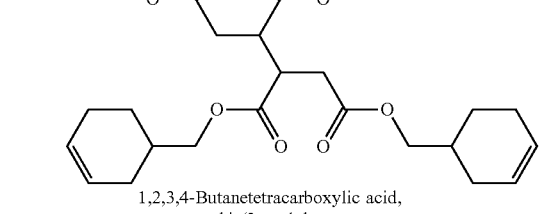

1,2,3,4-Butanetetracarboxylic acid,
tetrakis(3-cyclohexen-
1-ylmethyl)ester

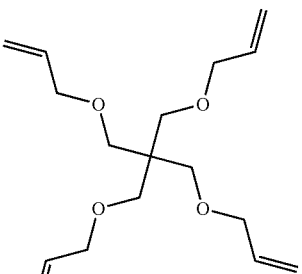

Tetraallyl pentaerythritol ether

The concentration of the olefin in solution may range from 1 to 99 wt %, preferably from 10 to 99 wt %, and most preferably from 20 to 80 wt %.

In an embodiment of the subject invention, the reaction temperature ranges from 0° C. to 110° C., preferably 30° C. to 100° C., and most preferably 50° C. to 100° C.

In an embodiment of the subject invention, the residence time of the reaction ranges from 10 seconds to 120 seconds, preferably 15 seconds to 100 seconds, and most preferably 20 seconds to 100 seconds.

In an embodiment of the subject invention, the reaction backpressure is not specifically limited. The "backpressure" recited herein refers to pressure for maintaining a solvent or reactant in liquid phase at different temperature.

In an embodiment of the subject invention, when the reaction achieves a conversion rate of the olefin compound higher than or equal to 99%, it can have a molar selectivity of diepoxide and polyepoxide higher than or equal to 80%, preferably higher than or equal to 90%, and most preferably higher than or equal to 95%.

In an embodiment of the subject invention, when the reaction achieves a conversion rate of the olefin compound higher than or equal to 99%, it can have a molar selectivity of monoepoxides lower than or equal to 5%, preferably lower than or equal to 3%, and most preferably lower than or equal to 1.5%.

In an embodiment of the subject invention, when the reaction achieves a conversion rate of the olefin compound higher than or equal to 99%, it can have a molar selectivity of hydrolysis lower than or equal to 15%, preferably lower than or equal to 10%, and most preferably lower than or equal to 5%.

EXAMPLES

The following examples will further illustrate the subject invention and should not to be construed as limitative. Without departing from the spirit of the subject invention, modifications and changes derived by persons of ordinary skill in the art based on the subject invention should be deemed covered by the scope of the subject invention.

GC and HPLC Analysis

After the epoxidation of olefin is performed according to the subject invention, the obtained product is placed in 2-butanol for gas chromatography (GC) analysis, in which mass of each component is measured with the integrated area based on the calibration curve, and further converted to mole number. The titration for measuring peracetic acid and hydrogen peroxide in the peracetic acid solution is performed according to the Guobiao Standard "GB 19104-2008 Peracetic Acid Solution." The high performance liquid chromatography (HPLC) analysis for measuring peracetic acid, hydrogen peroxide and acetic acid is performed based on the process disclosed in the lecture "Chinese Journal of Analytical Chemistry, October 2004; Vol. 32, No. 10, pp. 1329 to 1332," in which the amount of each component is measured with the integrated area based on the calibration curve.

GC Analysis Conditions
Apparatus: PerkinElmer AutoSystem
Detector: Flame Ionization Detector (FID)
Column: Agilent Tech HP-1 0.320 mm, length=50 M, film=1.05
Carrier gas: $N_2$ 20 psi
Inlet temperature: 220° C.
Detect region temperature: 280° C.
HPLC Analysis Conditions
Apparatus: Waters 600
Detector: Waters 2487 Dual λ. Absorbance Detector
Detect wavelength: 205 nm
Column: YMC-Pack ODS C18 L=150 mm, ID=6.0 mm
Column temperature: 40° C.
Mobile Phase: Water: Acetonitrile=82:18 (v.v)
Flow rate of mobile phase: 0.8 mL/min
Selectivity Measurement The olefin conversion rate, monoepoxide molar selectivity, diepoxide molar selectivity and hydrolyzate molar selectivity in the epoxidation of olefin are defined as follows. In the case where the consumed olefin compound foams non-corresponding monoepoxide or diepoxide, the product is deemed hydrolysate.

$$\text{Olefin conversion rate} = \frac{\text{Olefin mole number before reaction} - \text{Olefin mole number after reaction}}{\text{Olefin mole number before reaction}} \times 100\%$$

$$\text{Monoepoxide molar selectivity} = \frac{\text{Monoepoxide mole number formed after reaction}}{\text{Olefin mole number before reaction} - \text{Olefin mole number after reaction}} \times 100\%$$

$$\text{Diepoxide molar selectivity} = \frac{\text{Diepoxide mole number formed after reaction}}{\text{Olefin mole number before reaction} - \text{Olefin mole number after reaction}} \times 100\%$$

Hydrolysate molar selectivity =
100% − (Monoepoxide molar selectivity) − (Diepoxide molar selectivity)

Example 1

1431 ml of acetic acid and 1646 ml of 50 wt % hydrogen peroxide were placed in a 12 L glass reaction flask, maintained at 45° C.; 280 ml of concentrated sulfuric acid was added dropwise over a duration of 90 min; then the mixture was stirred for 30 min. Temperature was maintained at 45° C., pressure was reduced to 10 torr, and distillation was performed for 2 hours to obtain peracetic acid solution. The peracetic acid solution was titrated with potassium permanganate solution and sodium thiosulfate solution, and the amount of peracetic acid in the peracetic acid solution was measured at 58.5 wt % and the amount of hydrogen peroxide at 3.4 wt %. Through HPLC analysis, the amount of acetic acid in the peracetic acid solution was determined to be 11.7 wt %.

Sodium acetate was added to the peracetic acid solution to form a peracetic acid solution with 1.0 wt % sodium acetate. A 1.0 ml glass gastight syringe was fed with the solution and mounted to a syringe pump with a flow rate set to 6.65 μl/min. 3-cyclohexene-1-carboxylic acid, 3-cyclohexen-1-yl methyl ester (5.0 g) was mixed with toluene (10.0 g), and fed into another 1.0 ml glass gastight syringe, and then mounted to a syringe pump with a flow rate set to 8.35 gl/min The above two solutions were injected into a glass microreactor with an equivalent diameter of 0.2 mm, and heated to 90° C.; the reaction residue time was 40 sec. After 10 minutes of reaction, GC analysis was performed. The diolefin reactant conversion rate was 99.7%, the monoepoxide molar selectivity was 1.2%, the diepoxide molar selectivity was 95.8%, and the hydrolysate molar selectivity was 3.0%.

Examples 2 to 5

Examples 2 to 5 were prepared according to the procedure of Example 1, with the exception that the toluene in Example 1 was respectively replaced with acetone, 2-ethylhexanol, benzyl alcohol and acetonitrile. The results of GC analysis were shown in Table 1.

Comparative Examples 1 to 3

Comparative Examples 1 to 3 were prepared according to the procedure of Example 1, with the exception that the toluene in Example 1 was replaced with cyclohexane, methanol and ethanol. The results of GC analysis were shown in Table 1.

TABLE 1

|  | $\delta_{T, solvent}$ | Within $\delta_{T, product} \pm 6$ (within $18.4 \pm 6$) | $\delta_{H, solvent}$ | $\geq \delta_{H, product} - 6$ ($\geq 7.9 - 6$) | Olefin conversion rate | Monoepoxide molar selectivity | Diepoxide molar selectivity | Hydrolysate molar selectivity |
|---|---|---|---|---|---|---|---|---|
| Example 1 | 18.2 | Y | 2.0 | Y | 99.7% | 1.2% | 95.8% | 3.0% |
| Example 2 | 20.0 | Y | 7.0 | Y | 99.5% | 1.7% | 93.9% | 4.4% |
| Example 3 | 20.1 | Y | 11.8 | Y | 99.7% | 1.4% | 94.0% | 4.6% |
| Example 4 | 23.8 | Y | 13.7 | Y | 99.9% | 1.2% | 93.1% | 5.7% |
| Example 5 | 24.4 | Y | 6.1 | Y | 99.5% | 1.4% | 93.0% | 5.6% |
| Comparative Example 1 | 16.8 | Y | 0.2 | N | 90.3% | 30.2% | 66.5% | 3.3% |
| Comparative Example 2 | 26.5 | N | 19.4 | Y | 99.9% | 1.1% | 88.7% | 10.2% |
| Comparative Example 3 | 29.6 | N | 22.3 | Y | 99.7% | 1.3% | 86.8% | 11.9% |

Example 6

The 58.5 wt % peracetic acid solution in Example 1 was added to a sodium acetate solution to form a peracetic acid solution with 1.0 wt % sodium acetate and 43 wt % peracetic acid. The peracetic acid solution was fed into a 1.0 ml glass gastight syringe, and the syringe was mounted to a syringe pump with a flow rate set to 6.5 µl/min. 3-cyclohexene-1-carboxylic acid, 3-cyclohexen-1-yl methyl ester (3.0 g) was mixed with benzyl alcohol (2.0 g), and fed into another 1.0 ml glass gastight syringe, which was mounted to a syringe pump with a flow rate set to 5.5 µl/min.

The above two solutions were injected into a glass microreactor with an equivalent diameter of 0.2 mm, and heated to 90° C.; the reaction residue time was 50 sec. After 10 minutes of reaction, GC analysis was conducted. The diolefin reactant conversion rate was 99.6%, the monoepoxide molar selectivity was 0.7%, the diepoxide molar selectivity was 85.1%, and the hydrolysate molar selectivity was 14.2%.

Examples 7 and 8

Examples 7 and 8 were prepared according to the procedure of Example 6, with the exception that the benzyl alcohol in Example 6 was respectively replaced with ethyl acetate and ether/toluene (weight ratio=1:1) mixture solution. The results of GC analysis were shown in Table 2.

Comparative Examples 4 and 5

Comparative Examples 4 and 5 were prepared according to the procedure of Example 6, with the exception that the benzyl alcohol in Example 6 was respectively replaced with toluene/n-hexane (weight ratio=1:9) mixture solution and toluene/n-hexane (weight ratio=1:1) mixture solution. The results of GC analysis were shown in Table 2.

Example 9

The 58.5 wt % peracetic acid solution in Example 1 was added to a sodium acetate solution to form a peracetic acid solution with 1.0 wt % sodium acetate and 42 wt % peracetic acid. The peracetic acid solution was then fed into a 1.0 ml glass gastight syringe, and the syringe was mounted to a syringe pump with a flow rate set to 6.5 µl/min. 3-cyclohexene-1-carboxylic acid, 3-cyclohexen-1-yl methyl ester (2.5 g) was mixed with ethyl acetate (2.0 g), and fed into another 1.0 ml glass gastight syringe, which was mounted to a syringe pump with a flow rate set to 5.5 µl/min.

The above two solutions were injected into a glass microreactor with an equivalent diameter of 0.2 mm, and heated to 80° C.; the reaction residue time was 50 sec. After 10 minutes of reaction, GC analysis was performed. The diolefin reactant conversion rate was 99.7%, the monoepoxide molar selectivity was 1.2%, the diepoxide molar selectivity was 98.7%, and the hydrolysate molar selectivity was 0.1%.

Example 10

The 58.5 wt % peracetic acid solution in Example 1 was added to a sodium acetate solution to form a peracetic acid solution with 1.0 wt % sodium acetate and 42 wt % peracetic acid. The peracetic acid solution was then fed into a 25 ml syringe of a continuous duel syringe pump with a flow rate of 8.44 ml/min; 3-cyclohexene-1-carboxylic acid, 3-cyclohexen-1-yl methyl ester (250 g) was mixed with ethyl acetate (200 g), and fed into another syringe of the continuous duel syringe pump with a flow rate set to 7.16 ml/min.

The above two solutions were injected into a flow reactor with an equivalent diameter of 1.34 mm, and heated to 80° C.; the reaction residue time was 50 sec. After 30 minutes of

TABLE 2

|  | $\delta_{T, solvent}$ | Within $\delta_{T, product} \pm 6$ (within $18.4 \pm 6$) | $\delta_{H, solvent}$ | $\geq \delta_{H, product} - 6$ ($\geq 7.9 - 6$) | Olefin conversion rate | Monoepoxide molar selectivity | Diepoxide molar selectivity | Hydrolysate molar selectivity |
|---|---|---|---|---|---|---|---|---|
| Example 6 | 23.8 | Y | 13.7 | Y | 99.6% | 0.7% | 85.1% | 14.2% |
| Example 7 | 18.1 | Y | 7.2 | Y | 99.9% | 1.2% | 84.2% | 14.6% |
| Example 8 | 16.7 | Y | 3.3 | Y | 99.4% | 4.8% | 80.7% | 14.5% |
| Comparative Example 4 | 15.2 | Y | 0.2 | N | 97.0% | 11.5% | 75.9% | 12.6% |
| Comparative Example 5 | 16.5 | Y | 1.0 | N | 97.6% | 8.7% | 68.4% | 22.9% | reaction, GC analysis was performed. The diolefin reactant conversion rate was 99.9%, the monoepoxide molar selectivity was 0.3%, the diepoxide molar selectivity was 93.8%, and the hydrolysate molar selectivity was 5.9%.

Experiment Result

As shown in Table 1, $\delta_{T,solvent}$ and $\delta_{H,solvent}$ of the solvent in Examples 1 to 5 fall within the specific range defined by the subject invention, and thus Examples 1 to 5 achieve a high olefin conversion rate while maintaining a low monoepoxide molar selectivity and a low hydrolysate molar selectivity. Comparative Example 1 fails to have a $\delta_{H,solvent}$ falling within the specific range defined by the subject invention, and thus has a slower reaction rate of epoxidation; therefore, Comparative Example 1 has a lower conversion rate and a higher monoepoxide molar selectivity. Since $\delta_{T,solvent}$ of Comparative Examples 2 and 3 does not fall into the specific range defined by the subject invention, the ability of the solvent for preventing resins from being hydrolyzed is lower; therefore, Comparative Examples 2 and 3 have high conversion rates but also higher hydrolysate molar selectivity.

In view of Table 2, even if the residue time is longer, Comparative Examples 4 and 5 fail to achieve a conversion rate greater than 99%, and have relatively high monoepoxide molar selectivity and hydrolysate molar selectivity.

In view of Examples 9 and 10, it is found that the subject invention can be carried out with flow reactors with different passage inner diameter, and thus is suitable for industrial manufacturing.

Given the above, the examples of the subject invention using suitable solvent based on its solubility parameter can achieve a high olefin conversion rate and, simultaneously, a lower monoepoxide molar selectivity and hydrolysate molar selectivity.

We claim:

1. A process for the epoxidation of an olefin, comprising reacting a peroxide compound with the olefin in the presence of a solvent, wherein the solvent has Hansen Solubility Parameters (HSPs) of a total solubility parameter of $\delta_{T,solvent}$ and a hydrogen bonding force parameter $\delta_{H,solvent}$, and an epoxide product has HSPs of a total solubility parameter of $\delta_{T,product}$ and a hydrogen bonding force parameter of $\delta_{H,product}$, and wherein:

$\delta_{T,product}-6 \leq \delta_{T,solvent} \leq \delta_{T,solvent}+6$; and $\delta_{H,product}-6 \leq \delta_{H,solvent}$.

2. The process of claim 1, wherein:

$\delta_{T,product}-6 \leq \delta_{T,solvent} \leq \delta_{T,solvent}+3$; and $\delta_{H,product}-6 \leq \delta_{H,solvent}$.

3. The process of claim 1, wherein the peroxide is peroxy acid.

4. The process of claim 1, where in the reactor is a flow reactor.

5. The process of claim 4, where in the flow reactor is a micro-reactor.

6. The process of claim 5, wherein the flow reactor has an equivalent inner diameter of 0.01 mm to 10 mm.

7. The process of claim 5, wherein the flow reactor has a single passage, parallel passages or serial passages.

8. The process of claim 5, wherein, with respect to the olefin, the flow velocity of the peroxide is 0.2 to 5.

9. The process of claim 1, wherein, with respect to the olefin, the equivalence ratio of the peroxide is 0.5 to 3.

10. The process of claim 1, further comprising adding a buffer agent during reaction in an amount less than or equal to 5 wt %.

11. The process of claim 1, wherein the peroxide is added to the reactor in the form of a peroxide solution.

12. The process of claim 1, wherein the olefin is cycloaliphatic olefin.

13. The process of claim 1, wherein the concentration of the olefin in solution is 1 to 99 wt %.

14. The process of claim 1, wherein the reaction temperature is from 0° C. to 110° C.

15. The process of claim 1, wherein the residence time of the reaction is from 10 seconds to 120 seconds.

* * * * *